United States Patent [19]
Shindo

[11] Patent Number: 6,083,251
[45] Date of Patent: Jul. 4, 2000

[54] EYE TREATMENT METHOD AND APPARATUS

[76] Inventor: Kohei Shindo, No. 9-5, Hyakunincho 2-chome, Shinjuku-ku, Tokyo, Japan

[21] Appl. No.: 09/190,928

[22] Filed: Nov. 12, 1998

[30] Foreign Application Priority Data

Nov. 13, 1997 [JP] Japan ................................. 9-329593

[51] Int. Cl.[7] ............................................. A61N 1/36
[52] U.S. Cl. ............................................. 607/53
[58] Field of Search ........................ 607/53, 59, 139, 607/140, 141, 63

[56] References Cited

U.S. PATENT DOCUMENTS

| | | | |
|---|---|---|---|
| 3,527,230 | 9/1970 | Imamura | 607/53 |
| 4,331,163 | 5/1982 | Womura | 607/141 |
| 4,372,319 | 2/1983 | Chinomiya et al. | 607/63 |
| 4,603,697 | 8/1986 | Kamerling | 607/53 |
| 4,919,139 | 4/1990 | Brodard | 607/59 |

*Primary Examiner*—William E. Kamm
*Attorney, Agent, or Firm*—Hoffmann & Brown, LLP

[57] ABSTRACT

An eye treatment method and apparatus. The method including fitting a pair of electrodes to the temples around both the eyeballs. The temples are electrically stimulated by repeatedly imposing low-frequency signals having an output level that gradually increases from a substantial zero level and returns to the substantial zero level directly after reaching a maximum level each prescribed time on the electrodes. The apparatus includes a low-frequency signal generating means for generating low-frequency signals for electrically stimulating the ciliary muscle. Output control means is provided for causing the low-frequency signal generating means to repeatedly output the low-frequency signals in an output mode in which an output level gradually increases from the substantial zero level and returns to the substantial zero level directly after reaching the maximum level each prescribed time. The low-frequency signals are supplied to a pair of electrodes which may be fitted to the temples.

9 Claims, 7 Drawing Sheets

→ PASSED TIME

EYE TREATMENT METHOD AND APPARATUS

BACKGROUND OF THE INVENTION

The present invention relates to an eye treatment method and an eye treatment apparatus for restoring eyesight by electric stimulation.

Eyes form an image to the retina by the light reflected from an object through the cornea, the pupil, the crystalline lens and the vetreous body and send the signals of the image to the cerebrum through the optic nerve. The cerebrum recognizes the image signals sent thereto through the optic nerve as the sense of sight. When the eyes look at an object located near to it, the eyes largely refract light by thickening the crystalline lens by applying tension to the ciliary muscle of them, whereas when the eyes look at an object located far from it, they are focused on the object by reducing the refraction of light by making the thickness of the crystalline lens thin by recovering the ciliary muscle to which the tension has been applied. However, eyes cannot adjust the focal points of them well when they are in refractive myopia resulting from the refractive index of the cornea and crystalline lens which is larger than a usual refractive index, when they are in axial myopia resulting from an increase of length of eyeballs in the axial direction of light, when they are in refractive hyperopia resulting from the refractive index of the cornea and crystalline lens which is smaller than the usual refractive index, and when they are in axial hyperopia resulting from a decrease of length of eyeballs in the axial direction of light.

As a measure for the above problems, eyesight has been ordinarily corrected using eyeglasses or contact lenses. According to Japanese Unexamined Patent Publication No. 7-289649, however, there has been proposed an electric stimulation apparatus for stimulating the optic nerve. The electric stimulation apparatus stimulates the temples with low-frequency signals of 44 Hz to treat achromatopsia to blue and with low-frequency signals of 70 Hz to treat achromatopsia to red as well as stimulates points of the head located above 4–5 cm from the hairline with low-frequency signals of 3–10 Hz to recover eyesight. In this case, however, since electrodes covered with a moisture-keeping-material is used to reliably stimulate points of the head where hair grows for recovering eyesight, the electrode has a complex structure and using method thereof is troublesome.

SUMMARY OF THE INVENTION

An object of the present invention is to provide an eye treatment method and an eye treatment apparatus capable of simply performing electric stimulation to recover the deterioration of eyesight. Another object of the present invention is to provide a recording medium for treatment and a treatment system making use of a communication line on the premise that a personal computer is used to recover the deterioration of eyesight or visual acuity by electric stimulation not only by treatment performed in a clinic but also at home.

As a result of the diligent study made by the inventors of the present invention for a long time as to a electric stimulation method of recovering eyesight, the inventors have found a treatment method of fitting a pair of electrodes to the temples around eyeballs and electrically stimulating the ciliary muscle by repeatedly imposing low-frequency signals whose output level is made to substantially zero each prescribed time between the electrodes to achieve the above objects.

According to the present invention, there can be obtained a treatment effect for recovering eyesight in a high probability by electric stimulation to temples using low-frequency signals whose output level is repeatedly lowered in place of low-frequency signals having a simply continuous waveform. The invention is also effective to headache and stiff shoulders resulting from asthenopia and the optic nerve. In addition, a user can recover eyesight and the like making use of a computer even at home and so on by obtaining a recording medium. At the time, a simply arranged output converter can be connected to an earphone jack or low-frequency signals can be directly supplied to electrodes from speaker output terminals. Further, a program effective to treatment can be loaded on the computer of the user through a communication program for treatment.

DESCRIPTION OF THE PREFERRED EMBODIMENT

A treatment apparatus according to an embodiment of the present invention will be described with reference to FIG. 1 to FIG. 5.

Figure 2:
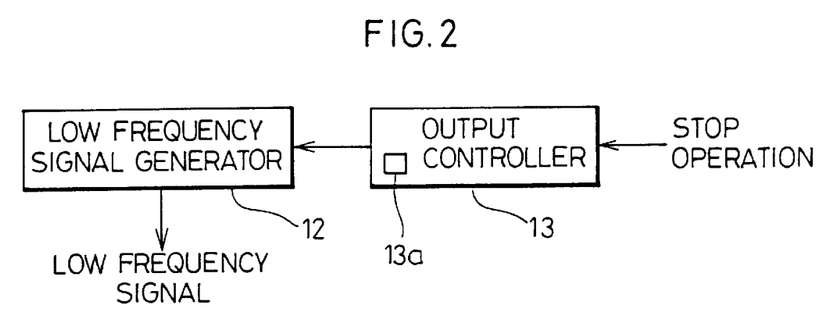
FIG. 2 is a block diagram describing an function of the personal computer.

FIG. 2 shows a basic arrangement of the treatment apparatus including a low-frequency signal generator 12 for generating low-frequency signals of 20 Hz which have a gradually increasing amplitude and are effective to stimulate the ciliary muscle and an output controller 13 for causing the low-frequency signal generator 12 to generate the low-frequency signals for a timer time Tc, for example, 20 minutes in an output mode in which the low-frequency signals are repeated for each prescribed time, for example, each 5 seconds and to stop the generation of the low-frequency signals in response to a stop operation.

Figure 1:
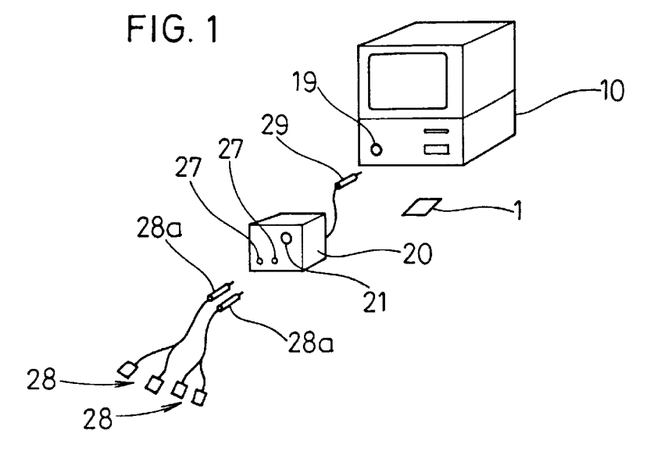
FIG. 1 is a view showing an arrangement of a treatment apparatus making use of a personal computer according to an embodiment of the present invention.

FIG. 1 shows a specific arrangement of the treatment apparatus which is composed of a general-purpose personal computer 10 having a programmable sound function, a recording medium 1 such as an FD, CD-ROM, etc. on which a program is recorded and a battery-driven-type output adapter 20 to which low-frequency signals are supplied from an earphone jack 19 for the sound output terminal of the personal computer 10 and from which the low-frequency signals are supplied to two pairs of electrodes 28.

The program recorded on the recording medium 1 includes signal output conditions and a processing procedure such as the frequency of sound output signals, the amplitude increment level Δ V of the sound output signals for each cycle, a maximum amplitude level Vmax, the timer time Tc, etc. Δ V is set such that it is added for each one cycle of 20 Hz and the Vmax is reached in the prescribed time of 5 seconds. A initial one cycle may be at a perfectly zero level in place of Δ V. The program is created such that treatment can be started and arbitrarily stopped on a screen by clicking an attached mouse. Since the CPU of the personal computer 10 operates in accordance with the program arranged as described above, it constitutes the output controller 13 in cooperation with the incorporated timer; and it constitutes the low-frequency signal generator 12 in cooperation with a sound source and a sound circuit for outputting analog signals subjected to A/D conversion.

Figure 3:
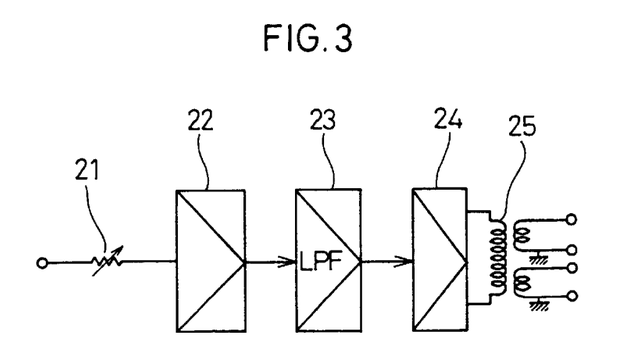
FIG. 3 is a block diagram showing a circuit arrangement of an output adapter attached to the personal computer.
Figure 4:
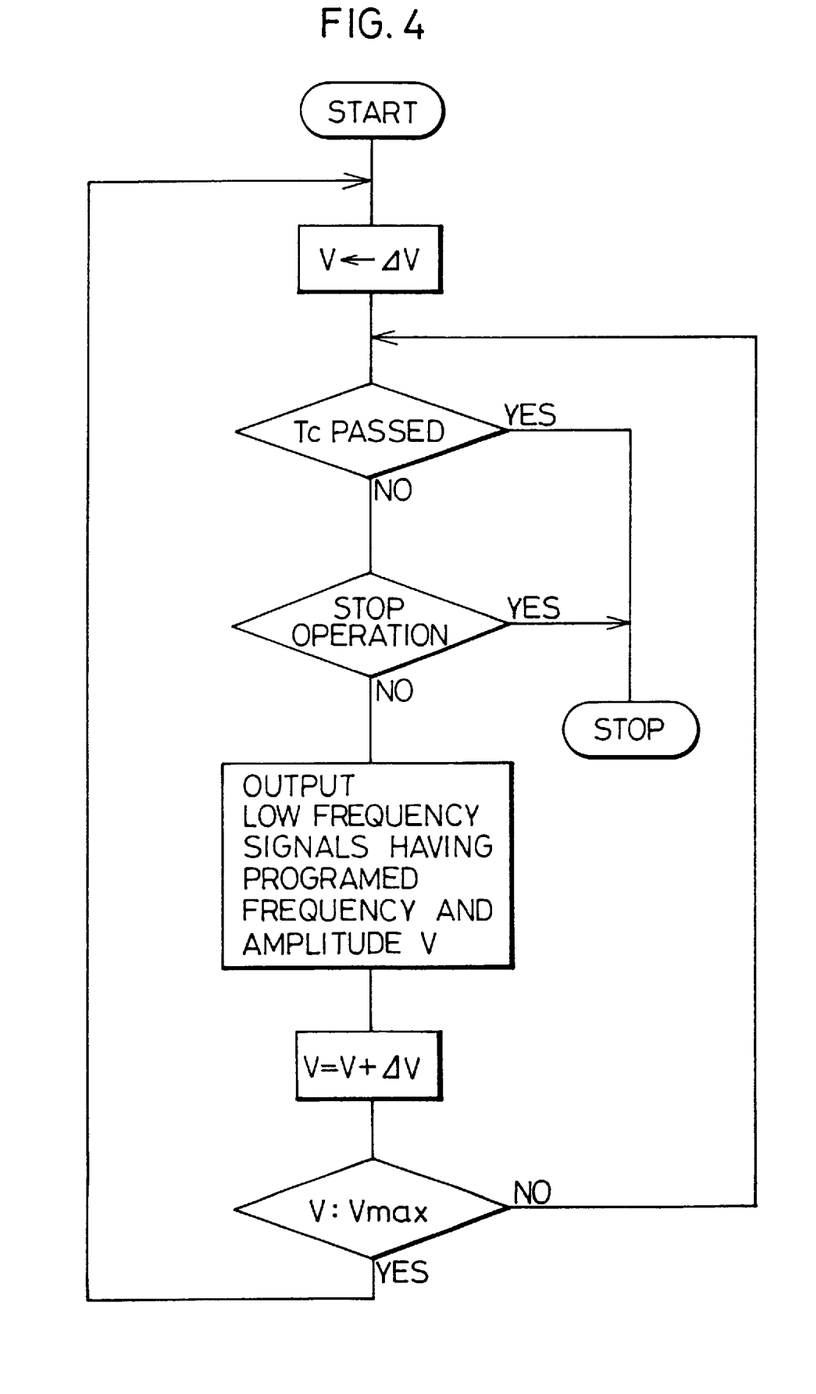
FIG. 4 is a flowchart describing an operation of the personal computer.

As shown in FIG. 3, the output adapter 20 includes an amplitude adjusting volume 21, a preamplifier 22, a lowpass filter 23 for removing noise having a frequency component higher than the low-frequency signals of 20 Hz, a main amplifier 24 and a transformer 25 for outputting two-channel low-frequency signals to the right and left eyes in order to process the low-frequency signals supplied to the output adapter 20 through a plug 29 inserted into the earphone jack 19. The output terminals of the output adapter 20 are connected to output terminal jacks 27 into which plugs 28a connected to electrodes 28 are inserted. The voltage outputted from the electrodes is set such that a current from skin is made to about 10 mA at a maximum.

The user of the personal computer 10 for treatment obtains the output adapter 20 to which the electrodes 28 are attached and the recording medium 1, sets the recording medium 1 to the personal computer 10 and causes the personal computer 10 to previously read out the program stored in the recording medium 1 to the program memory of the personal computer 10. Further, the user arranges the menu screen of the personal computer 10 so that treatment can be selected thereon. To use the treatment apparatus, the user sets the plug 29 of the output adapter 20 to the earphone jack 19 of the personal computer 10 and fits the electrodes 28 to temples around the right and left eyes, respectively. When the user clicks treatment on the menu screen and then clicks a display of start on a displayed screen, the personal computer 10 starts operation according to the flowchart shown in FIG. 4.

Figure 5:
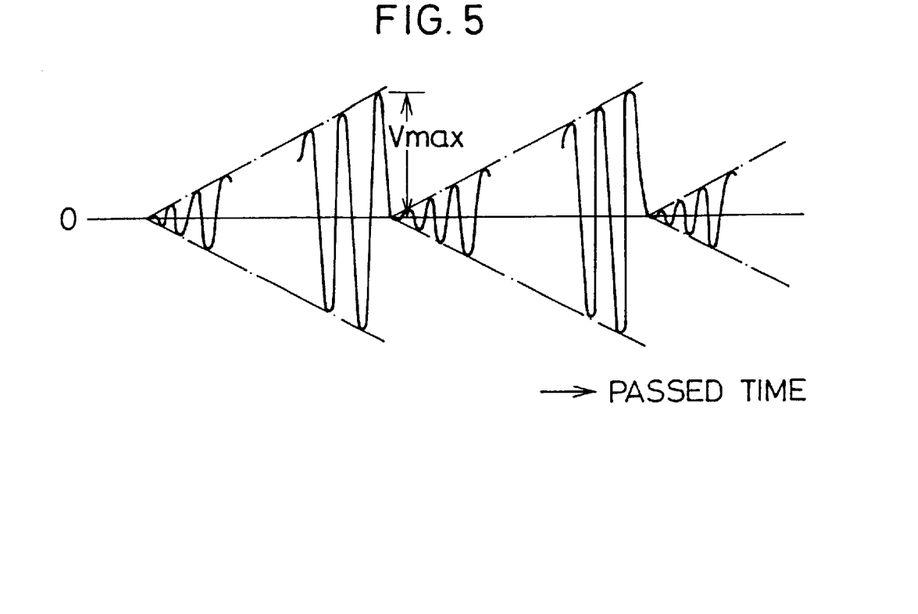
FIG. 5 is a waveform view of a low-frequency signal supplied to electrodes from the output adapter.

With this operation, low-frequency analog signals whose amplitude is gradually increased by Δ V each cycle and which have a pattern in which an envelope curve is formed to a saw-tooth shape are supplied to the electrodes 28 after they are amplified as shown in FIG. 5. When the low-frequency signals reach the maximum output level Vmax in a prescribed time, their level returns to the minute output level Δ V and thereafter gradually increases again. The electric stimulation, which is performed in such a dynamic output mode that the level of the low-frequency signals gradually increases each prescribed time from the substantially zero level at which almost no treatment effect is obtained, can enhance a treatment effect as compared with the treatment performed by simply continuous low-frequency signals. In particular, the gradual increase of the output level of the low-frequency signals can activate the cells. When 20 minutes elapse, the treatment is automatically stopped, otherwise it can be arbitrarily stopped by clicking a display of stop on the screen. An output current can be adjusted by the volume 21 so that no unpleasant feeling is caused.

The effect achieved by the treatment apparatus for recovering eyesight in such a described manner as dynamic and gradually increasing stimulation has been confirmed by many subjects. Although the effect is different depending upon respective subjects, when a subject of moyopia having eyesight of, for example, about 0.03 is subjected to the treatment 10 times for each 20 minutes at a pace of two times a week, his or her eyesight will be recovered to about 0.08 and further to about 0.5 when he or she is subjected to the treatment 30 times, on average. In addition, it has been also confirmed that the treatment apparatus is also effective to asthenopia, stiff shoulders caused thereby and the like. The treatment is also effective to hyperopia, although it is not so remarkable to myopia.

Figure 6A:
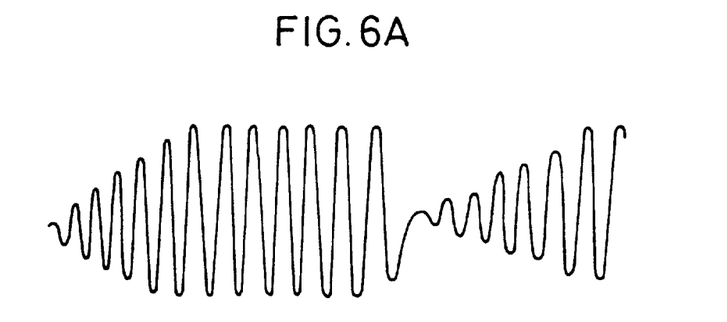
FIGS. 6A and 6B are waveform views showing low-frequency signals in another embodiment.
Figure 6B:
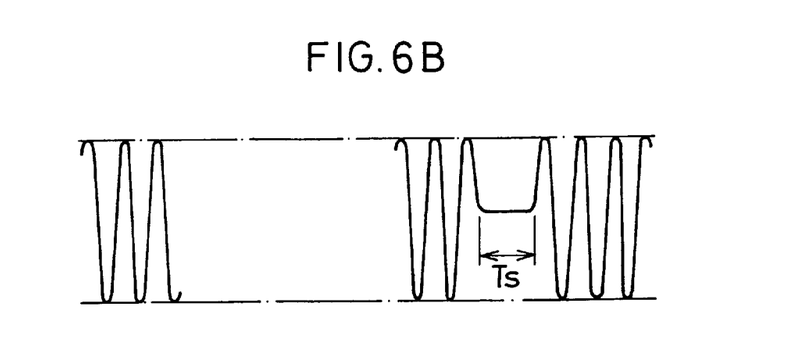

Although the low-frequency signals are effective in the frequency range of about 1 Hz to 100 Hz, it has been confirmed that their effect is remarkable in the range of 10 Hz to 40 Hz which is near to the aforesaid 20 Hz. It is preferable that the low-frequency signals are repeated at a cycle of about 3 seconds to 10 seconds. In particular, the low-frequency signals having the saw-tooth-shaped bipolar envelop have a remarkable effect. It is also conceived that the low-frequency signals have such a dynamic pattern that their amplitude is made constant after it is gradually increased as shown in FIG. 6A; otherwise the low-frequency signals have such an dynamic output mode that a constant amplitude is continued for about 5 seconds and repeated after a pause Ts of about 1 second as shown in FIG. 6B.

As described above, the recording medium 1 and the output adapter 20 to which the electrodes 28 are attached can be sold or rented as a personal treatment apparatus on the premise that the apparatus is used in combination with a personal computer. Further, as another embodiment, when a personal computer has two pairs of speaker output terminals, a program can be created so that amplified low-frequency signals are supplied to the pairs of right and left electrodes without the provision of the above output adapter. When only one speaker output terminal is available, it is possible to connect a pair of electrodes or two pairs of electrodes in parallel with each other. In this case, the treatment apparatus is composed only of the recording medium and the electrodes. The treatment apparatus mentioned above can be also used in a clinic and further may be arranged as a dedicated treatment apparatus using a digital or an analog circuit.

Figure 7:
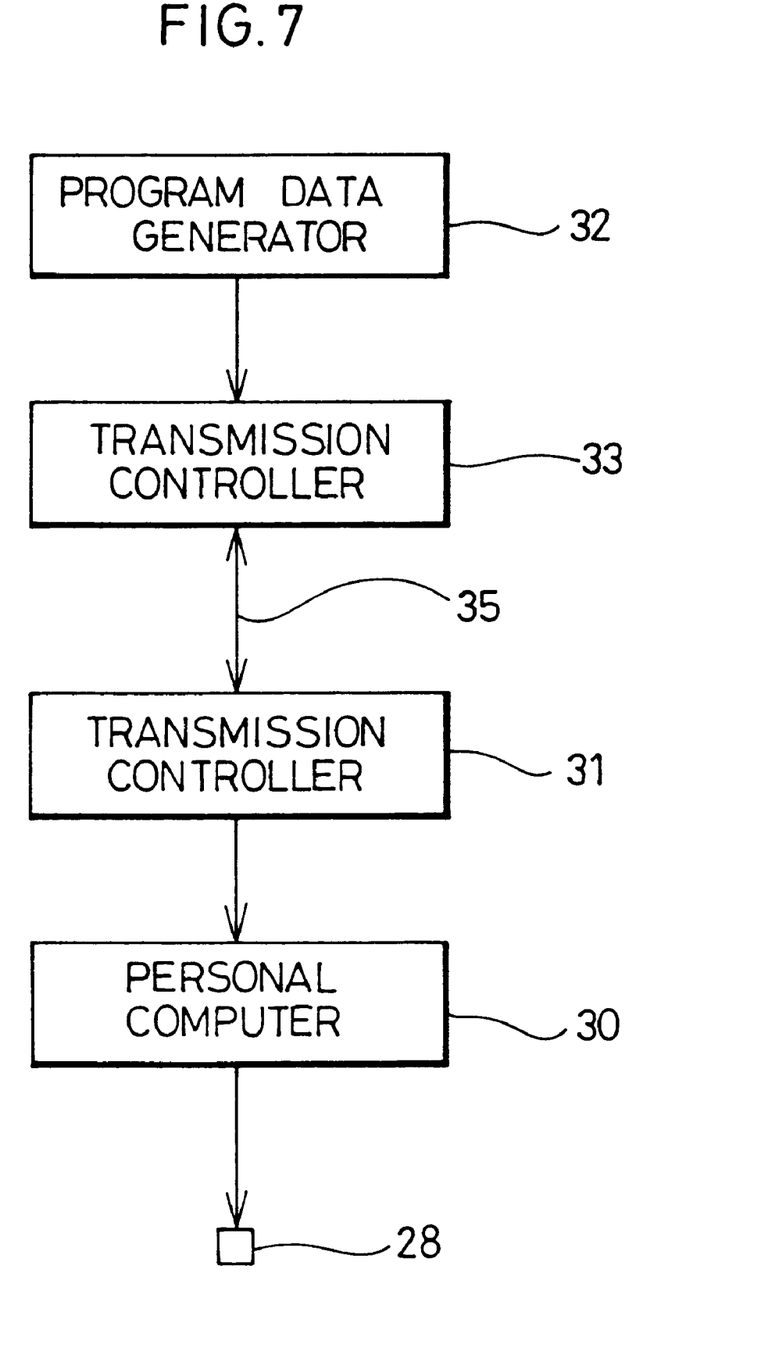
FIG. 7 is a block diagram showing an arrangement of a treatment system according to an embodiment of the present invention.

The aforesaid treatment program can be transmitted through a system composed making use of a communication line shown in FIG. 7. More specifically, a provider of the program prepares on his side a program data generator 32 for generating program data for causing a personal computer 30 to function as a low-frequency-signal generator for generating low-frequency signals for electrically stimulating the ciliary muscle and an output a low-frequency-signal generator for generating low-frequency signals for electrically stimulating the ciliary muscle, a program data generator 32 for generating program data for causing a personal computer 30 to function as an output controller which causes the low-frequency-signal generator to repeatedly output the low-frequency signals in an output mode in which an output level is lowered at each prescribed time and a transmission controller 33 for transmitting the program data through a communication line 35 in association with a modem. A user of the system loads the program data on the personal computer 30 by connecting the personal computer 30 to which a transmission controller 31 is attached to the system of the provider of the program through the communication line 35 and performs treatment by connecting the electrodes 28 to speaker terminals or connecting an output adapter to an earphone jack.

FIG. 8 to FIG. 11 show a dedicated treatment apparatus according to another embodiment using a microcomputer which constitutes the low-frequency signal generator 12 and the output controller 13 shown in FIG. 2. The low-frequency signal generator 12 is composed of a microcomputer 40 including a CPU 40a, a ROM 40b in which a program for operating the CPU 40a is stored, a RAM 40c having a working area, an I/O port 40d, a timer 40e and the like, a D/A converter 41 composed of a ladder network having resistor R and a resistor 2R which are combined with each other and a lowpass filter 42.

Figure 8:
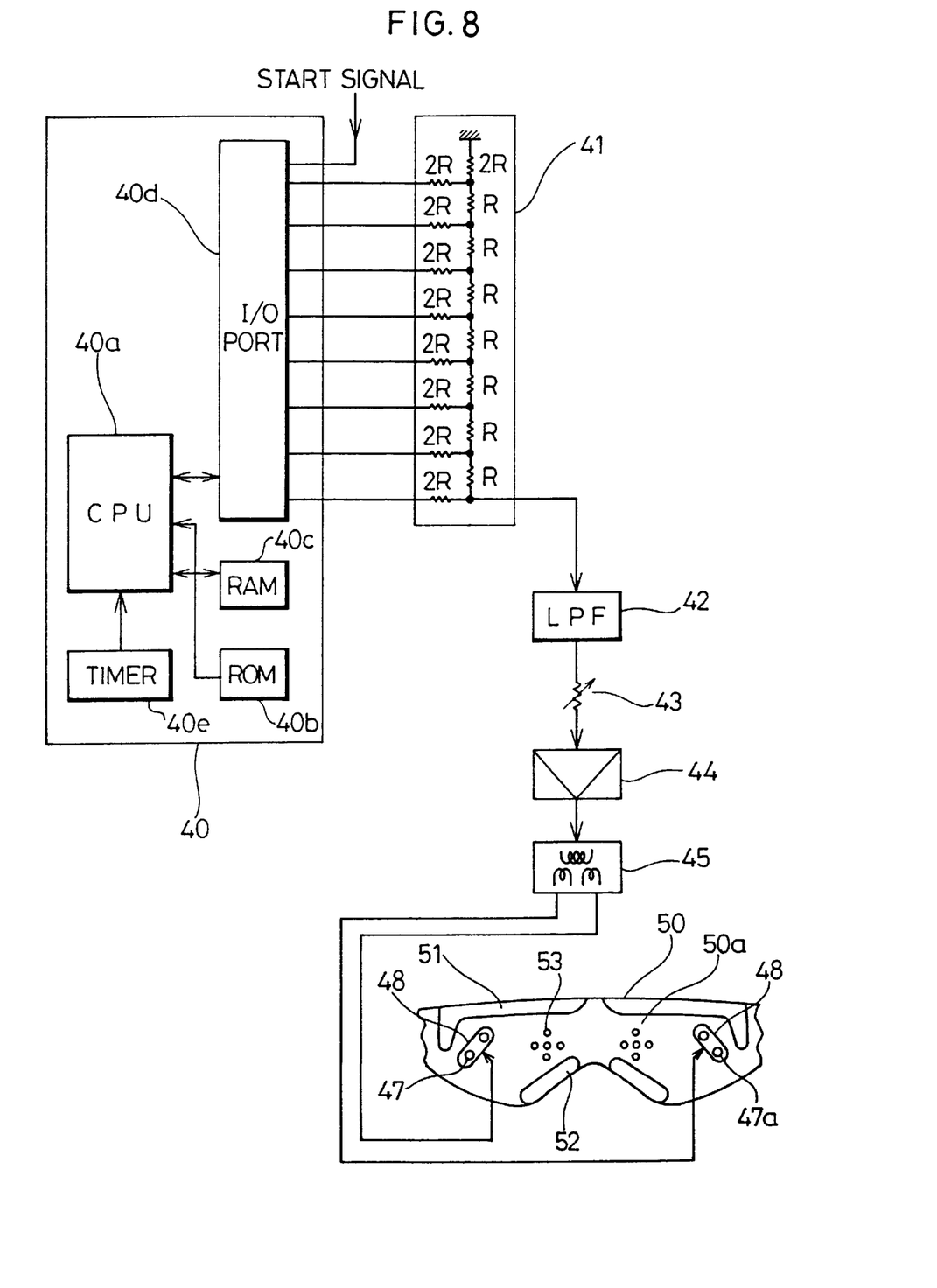
FIG. 8 is a block diagram showing an eye treatment apparatus according to another embodiment.
Figure 9:
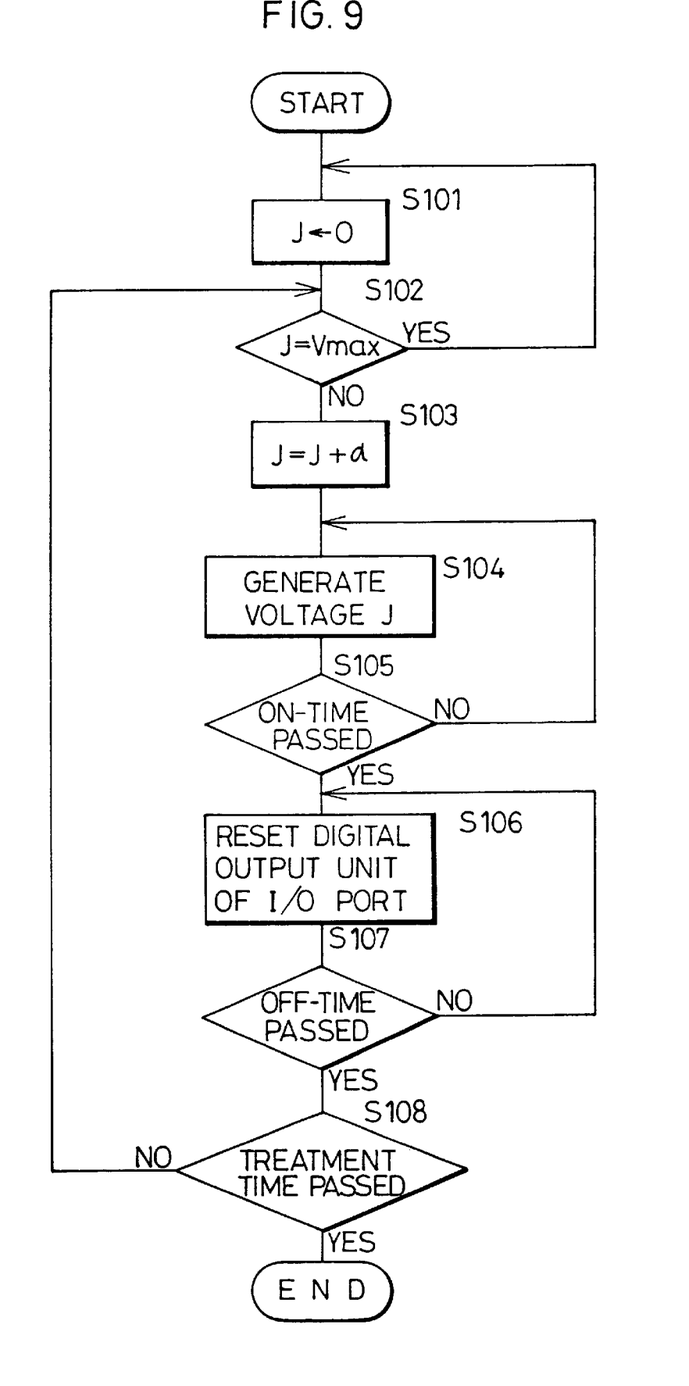
FIG. 9 is a flowchart describing an operation of the treatment apparatus shown in FIG. 8.

The CPU 40a operates as follows in accordance with the program stored in the ROM 40b and the flowchart shown in FIG. 9. Zero is set to a not shown register J in response to a start signal (step S101). It is determined whether the value of the register J has reached a maximum voltage value Vmax or not (step S102). When it has not reached the maximum voltage value Vmax, a prescribed value a is added to the register J (step S103) and the I/O port 40d is operated to a state corresponding to the value of the register J (step S104). With this operation, a voltage corresponding to the value of the register J is output from the D/A converter 41. The timer 40e determines whether an on-time Ton, for example, 25 ms, has passed or not. When the CPU 40a determines that the on-time Ton has passed from the timer 40e, all the digital outputs from the I/O port 40d are turned off (step S106). The timer 40e determines whether an off-time Toff of 25 ms has passed or not (step S107). When the timer 40e determines that the off-time Toff has passed, it further determines whether a treatment time Tt has passed or not (step S108). When the timer 40e determines that the treatment time Tt has not passed, the process returns to step S102 again.

Figure 10:
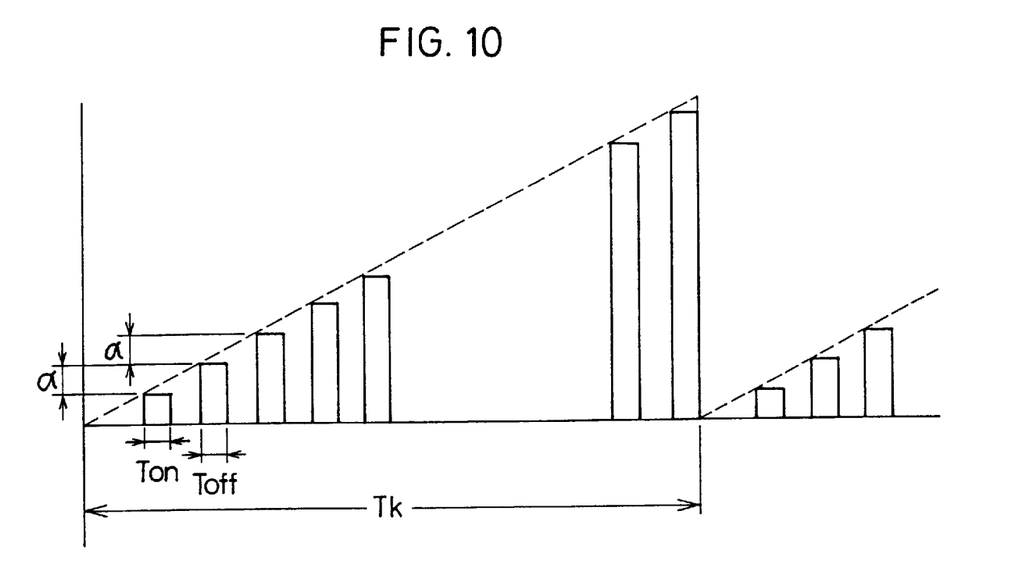
FIG. 10 is a view describing an operation waveform of the treatment apparatus shown in FIG. 8.

The D/A converter 41 generates pulse signals having the gradually increasing amplitude shown in FIG. 10. The repetition of the above steps permits the pulse signals to repeat such a cycle that a voltage is gradually increased as a time passes and returned to zero when a prescribed time Tk is reached at Vmax. Since an unnecessary component is removed from the thus generated pulse signals having the saw-tooth-shaped envelop curve by the lowpass filter 42, low-frequency signals, which have such a pattern that both the polarities of 20 Hz are gradually increased in correspondence to the on-time Ton and the off-time Toff, are generated as shown in FIG. 5.

Figure 11:
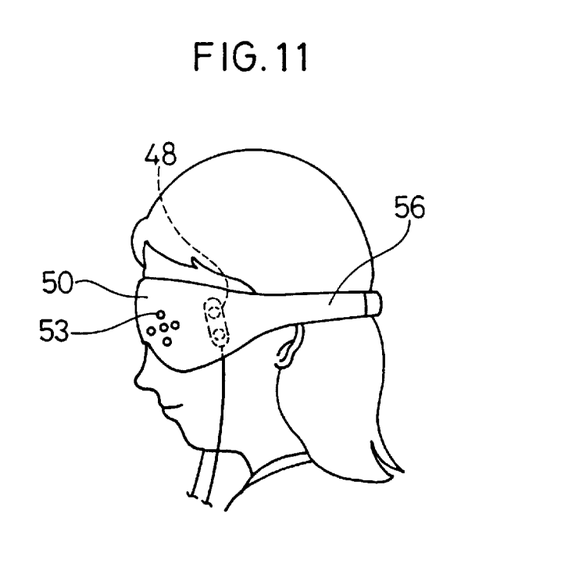
FIG. 11 is a side elevational view describing how the head band of the treatment apparatus shown in FIG. 8 is fitted.

In FIG. 8, numeral 50 denotes a head band to be mounted on a head for fitting two pairs of electrodes 47, 47a. The head band 50 has eye holes 53 and pads 51, 52 disposed on a front plate 50a. Further, plate-shaped belts 56 are attached to both the ends of the head band 50. A pair of the electrodes 47 and a pair of electrodes 47a are attached to two base plates 48, respectively. Each unit electrode has a diameter of about 10 mm and each pair of the electrodes are disposed in correspondence to two stimulation points of each temple with their centers spaced apart from each other by 25 mm. The base plates 48 are adhered to the front plate 50a after their positions are adjusted so that they confront the stimulation points of a patient.

In treatment, the base plates 48 are adhered to the front plate 50a so that the electrodes 47, 47a confront the temples of the patient, the front plate 50a is fitted to both the eyes and both the ends of the belts 56 are connected to each other on the rear side of the head. Amplified low-frequency signals are supplied to the electrodes 47, 47a through a transformer 45 in response to a start signal after the amount of stimulation applied by the low-frequency signals is adjusted by a variable resistor 43 to prevent uncomfortable stimulation from being applied to the patient. The low-frequency signals are output from the transformer 45 so that a voltage of the same polarity is imposed on the upper unit electrodes and lower unit electrodes of the electrodes 47, 47a. With this operation, the ciliary muscle is electrically stimulated at the right and left temples until the treatment time Tt set by the timer 40e passes. Accordingly, eyesight can be recovered and asthenopia, stiff shoulders caused by eyes and headache can be effectively treated only by mounting the head band on a head without the need of adhering electrodes from which lead wires extend to the temples.

What is claimed is:

1. An eye treatment method, comprising the steps of:
   fitting a pair of electrodes to the temples around both eyeballs; and
   electrically stimulating the temples by repeatedly imposing a low-frequency signal on the electrodes, the low frequency signal having an output level that gradually increases from a substantially zero level to a maximum level and directly returns to said substantially zero level each prescribed time.

2. An eye treatment method according to claim 1, further including the step of generating low-frequency signals including a sinusoidal wave of 10–40 Hz having an amplitude that gradually increases from a substantially zero level to a maximum level and directly returns to said substantially zero level each prescribed time of 3–10 seconds.

3. An eye treatment method according to claim 1, further including the step of attaching the pair of electrodes are attached to a head band to be set to the head of a patient at the positions confronting both the temples.

4. An eye treatment apparatus, comprising:
   low-frequency signal generating means for generating low-frequency signals for electrically stimulating the ciliary muscle;
   output control means for causing said low-frequency signal generating means to repeatedly output the low-frequency signals in an output mode in which an output level gradually increases from a substantially zero level to a maximum level and directly returns to said substantially zero level each prescribed time; and
   at least a pair of electrodes which are fitted to the temples and to which the low-frequency signals are supplied.

5. An eye treatment apparatus according to claim 4, wherein the low-frequency generating means and said output control means includes a computer and a recording medium that can be read by the computer, the recording medium including a program for causing the personal computer to generate and control the low-frequency signals for electrically stimulating the temples.

6. An eye treatment recording medium according to claim 5, further including an output adapter for amplifying the low-frequency signals supplied from earphone output terminals of the personal computer, the output adapter supplying amplified outputs to the pair of electrodes.

7. An eye treatment recording medium according to claim 5, wherein low-frequency signals are supplied from speaker output terminals of the personal computer to the pair of electrodes.

8. An eye treatment apparatus comprising:
   low-frequency signal generating means for generating low-frequency signals for electrically stimulating the ciliary muscle, said low-frequency generating means being composed of a microcomputer for generating digital signals corresponding to a gradually increasing amplitude in a low-frequency cycle, a D/A converter for converting the digital signals to analog and a lowpass filter for extracting a sinusoidal wave of the low-frequency cycle from the thus converted analog signals;

output control means for causing said low-frequency signal generating means to repeatedly output the low-frequency signals in an output mode in which an output level is lowered each prescribed time; and at least a pair of electrodes which are fitted to the temples and to which the low-frequency signals are supplied.

9. An eye treatment system comprising:

a computer;

program data generating means for generating program data for causing the the computer to function as low-frequency signal generating means for generating a low-frequency signal for electrically stimulating the ciliary muscle, and causing the computer to function as an output control means, the computer causing an output level of the low-frequency signal to gradually increase from a substantially zero level to a maximum level and directly returns to said substantially zero level each prescribed time;

transmission control means for transmitting the program data through a communication line so that the program data is read by the computer; and a pair of electrodes adapted to be fitted to the temples and operatively connected to the computer, the pair of electrodes supplying the low frequency signal to the temples.

* * * * *